United States Patent
Neumann

(10) Patent No.: US 11,928,561 B2
(45) Date of Patent: Mar. 12, 2024

(54) METHODS AND SYSTEMS FOR GROUPING INFORMED ADVISOR PAIRINGS

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 795 days.

(21) Appl. No.: 16/948,102

(22) Filed: Sep. 3, 2020

(65) Prior Publication Data

US 2021/0201199 A1 Jul. 1, 2021

Related U.S. Application Data

(63) Continuation-in-part of application No. 16/727,088, filed on Dec. 26, 2019, now Pat. No. 10,854,336.

(51) Int. Cl.

| | |
|---|---|
| *G16H 50/20* | (2018.01) |
| *A61B 5/00* | (2006.01) |
| *G06N 5/04* | (2023.01) |
| *G06N 20/00* | (2019.01) |
| *G06Q 30/0204* | (2023.01) |
| *G06Q 30/0282* | (2023.01) |
| *G16H 40/67* | (2018.01) |
| *G16H 50/30* | (2018.01) |

(52) U.S. Cl.
CPC ........... *G06N 20/00* (2019.01); *A61B 5/7267* (2013.01); *G06N 5/04* (2013.01); *G06Q 30/0204* (2013.01); *G06Q 30/0282* (2013.01); *G16H 40/67* (2018.01); *G16H 50/20* (2018.01); *G16H 50/30* (2018.01)

(58) Field of Classification Search
None
See application file for complete search history.

(56) References Cited

U.S. PATENT DOCUMENTS

| 8,095,389 B2 | 1/2012 | Dalton et al. |
| 8,655,682 B2 | 2/2014 | Srivastava et al. |
| 9,297,723 B1 * | 3/2016 | Hofmann ............... G06N 20/00 |

(Continued)

OTHER PUBLICATIONS

Han et al., A Hybrid Recommender System for PatientDoctor Matchmaking in Primary Care, Doctor Matchmaking in Primary Care 2018 IEEE 5th International Conference on Data Science and Advanced Analytics, Oct. 1, 2018, pp. 481-490, IEEE.

(Continued)

*Primary Examiner* — Robert A Sorey
(74) *Attorney, Agent, or Firm* — Caldwell Intellectual Property Law

(57) ABSTRACT

A system for customizing informed advisor pairings, the system including a computing device. The computing device is configured to identify a user feature wherein the user feature contains a user biological extraction. The computing device is configured to generate using element training data and using a first machine-learning algorithm a first machine-learning model that outputs advisor elements. The computing device receives an informed advisor element relating to an informed advisor. The computing device determines using output advisor elements whether an informed advisor is compatible for a user.

18 Claims, 7 Drawing Sheets

(56) References Cited

U.S. PATENT DOCUMENTS

| | | |
|---|---|---|
| 2005/0004815 A1* | 1/2005 | Machtelinck ........ G06Q 10/109 |
| | | 705/2 |
| 2010/0211411 A1 | 8/2010 | Hudson |
| 2010/0235178 A1 | 9/2010 | Firminger et al. |
| 2016/0224760 A1 | 8/2016 | Petak et al. |
| 2017/0039344 A1 | 2/2017 | Bitran et al. |
| 2017/0199189 A1 | 7/2017 | Wade |
| 2018/0119137 A1 | 5/2018 | Matsuguchi et al. |
| 2018/0322941 A1 | 11/2018 | Krishnan et al. |
| 2018/0365562 A1* | 12/2018 | Volkova ................... G06N 7/01 |
| 2019/0221303 A1 | 7/2019 | Bennett |
| 2020/0020454 A1* | 1/2020 | McGarvey ............. G16H 10/60 |

OTHER PUBLICATIONS

Sahoo et al., DeepReco: Deep Learning Based Health Recommender System Using Collaborative Filtering, Computation 2019 (Journal), May 22, 2019, article 25, vol. 7 issue 2, MDPI.

Baldominos, et al., DataCare: Big Data Analytics Solution for Intelligent Healthcare Management, International Journal of Interactive Multimedia & Artificial Intelligence, Mar. 20, 2017, pp. 13-20, vol. 4 No. 7, UNIR.

\* cited by examiner

METHODS AND SYSTEMS FOR GROUPING INFORMED ADVISOR PAIRINGS

CROSS-REFERENCE TO RELATED APPLICATIONS

This application is a continuation-in-part of Non-provisional application Ser. No. 16/727,088 filed on Dec. 26, 2019 and entitled "METHODS AND SYSTEMS FOR CUSTOMIZING INFORMED ADVISOR PAIRINGS," the entirety of which is incorporated herein by reference in its entirety.

FIELD OF THE INVENTION

The present invention generally relates to the field of artificial intelligence. In particular, the present invention is directed to methods and systems for grouping informed advisor pairings.

BACKGROUND

Locating an informed advisor who can resolve one or more issues and put a user at ease can be challenging. This is further complicated by user frustration in finding an informed advisor that is suitable for a plethora of reasons. This can be further burdened by an inundation of conflicting viewpoints and opinions of informed advisors among a variety of fields.

SUMMARY OF THE DISCLOSURE

In an aspect, a system for grouping informed advisor pairings includes a computing device, the computing device further configured to obtain a user feature. The computing device further configured to receive an informed advisor element relating an informed advisor to the user feature. The computing device further configured to generate an informed advisor grouping element as a function of the informed advisor element, wherein generating further comprises receiving a grouping training set relating an informed advisor to an advisor review score and computing the informed advisor grouping element as a function of the grouping training set using an advisor machine-learning process. The computing device further configured to determine a group compatible element as a function of the informed advisor grouping element. The computing device further configured to group informed advisors as a function of the group compatible element to enhance the user feature.

In an aspect, a method of grouping informed advisor pairings. The method includes obtaining by a computing device a user feature. The method further comprising receiving, by a computing device, an informed advisor element relating an informed advisor to the user feature. The method further comprising generating, by the computing device, an informed advisor grouping element as a function of the informed advisor element, wherein generating further comprises receiving a grouping training set relating an informed advisor to an advisor review score and computing the informed advisor grouping element as a function of the grouping training set using an advisor machine-learning process. The method further comprising, by the computing device, determining a group compatible element as a function of the informed advisor grouping element. The method further comprising, by the computing device, grouping informed advisors as a function of the group compatible element to enhance the user feature.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for grouping advisor pairings. In an embodiment, a computing device utilizes a user feature to group informed advisors to enhance a user feature. In an embodiment, a biological extraction may be a user feature. A computing device generates an informed advisor grouping element as an output, wherein an informed advisor element is an input. A computing device determines a group compatible element as a function of the informed advisor grouping element. A computing device groups informed advisors based on a group compatible element pairing informed advisors to enhance a user feature.

Figure 1:
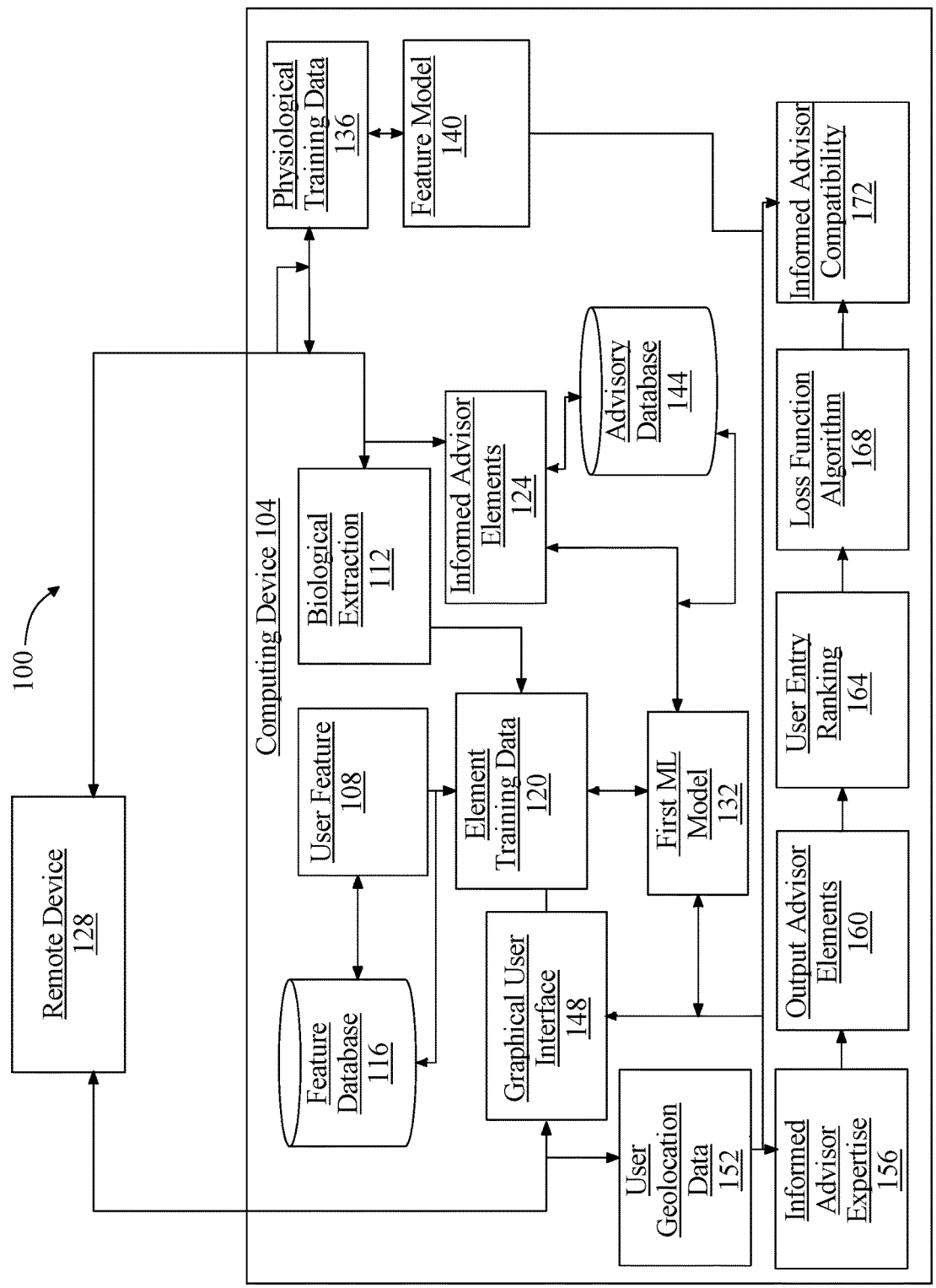
FIG. 1 is a block diagram illustrating an exemplary embodiment of a system for customizing informed advisor selection.

Referring now to FIG. 1, an exemplary embodiment of a system 100 for customizing informed advisor pairings is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to identify a user feature 108. A "user feature," as used in this disclosure, is a characteristic uniquely belonging to a human subject. A user feature 108 may include a particular trait, quality, behavior, and/or biological extraction that is specific to a particular human subject. A trait may include for example, positive qualities and characteristics such as love, joy, peace, patience, kindness, goodness, faithfulness, gentleness, truthfulness, loyalty, and self-control. A trait may include for example, negative qualities and characteristics such as sexual immorality, idolatry, debauchery, hatred, and jealousy. A trait may include a negative or problematic behavior such as an addition to a chemical substance, including an addiction to narcotics, stimulants such as cocaine, cocaine derivatives, amphetamines, methamphetamine, nicotine, or the like, opiates such as heroine, fentanyl, oxycodone, or the like, *cannabis, cannabis*-derived compounds such as THC, depressants such as alcohol, barbiturates, benzodiazepines, or the like, MDMA, PCP, hallucinogens such as LSD, addictions to any of various prescription drugs, or the like. As a further non-limiting example, a negative behavior may include an addition to an act, such as a gambling addition, a sex addiction characterized by compulsive engagement in sexual activity, a pornography addiction characterized by compulsive sexual activity concurrent with pornography consumption, gaming disorder characterized by compulsive use of Internet or video games, gambling addiction and/or problem gambling as characterized by compulsive or continuous gambling despite resulting financial harm, food addiction as characterized by compulsive overeating, an eating disorder such as anorexia or bulimia, or the like.

With continued reference to FIG. 1, a user feature 108 includes a user biological extraction 112. In an embodiment, a user trait may be a biological extraction 112. A "biological extraction" as used in this disclosure includes at least an element of user biological data. As used in this disclosure, "biological data" is any data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, biological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cell s, T-cells, Natural Killer Cells, and the like, absolute numbers of monocytes including macrophage precursors, absolute numbers of eosinophils, and/or absolute counts of basophils. Biological state data may include, without limitation, immune function data such as Interleukine-6 (IL-6), TNF-alpha, systemic inflammatory cytokines, and the like.

Continuing to refer to FIG. 1, biological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Biological state data may include measures of glucose metabolism such as fasting glucose levels and/or hemoglobin A1-C (HbA1c) levels. Biological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Biological state data may include measures of estimated glomerular filtration rate (eGFR). Biological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Biological state data may include antinuclear antibody levels. Biological state data may include aluminum levels. Biological state data may include arsenic levels. Biological state data may include levels of fibrinogen, plasma cystatin C, and/or brain natriuretic peptide.

Continuing to refer to FIG. 1, biological state data may include measures of lung function such as forced expiratory volume, one second (FEV-1) which measures how much air can be exhaled in one second following a deep inhalation, forced vital capacity (FVC), which measures the volume of air that may be contained in the lungs. Biological state data may include a measurement blood pressure, including without limitation systolic and diastolic blood pressure. Biological state data may include a measure of waist circumference. Biological state data may include body mass index (BMI). Biological state data may include one or more measures of bone mass and/or density such as dual-energy x-ray absorptiometry. Biological state data may include one or more measures of muscle mass. Biological state data may include one or more measures of physical capability such as without limitation measures of grip strength, evaluations of standing balance, evaluations of gait speed, pegboard tests, timed up and go tests, and/or chair rising tests.

Still viewing FIG. 1, biological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Biological state data may include one or more evaluations of sensory ability, including measures of audition, vision, olfaction, gustation, vestibular function, and pain.

Continuing to refer to FIG. 1, biological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, biological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Biological state data may include proteomic data, which as used herein is data describing all proteins produced and/or modified by an organism, colony of organisms, or system of organisms, and/or a subset thereof. Biological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other biological state data of a person, as described in further detail below.

With continuing reference to FIG. 1, biological state data may include one or more user-entered descriptions of a person's biological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Biological state data may include any biological state data, as described above, describing any multicellular organism living in or on a person including any parasitic and/or symbiotic organisms living in or on the persons; non-limiting examples may include mites, nematodes, flatworms, or the like. Examples of biological state data described in this disclosure are presented for illustrative purposes only and are not meant to be exhaustive.

With continued reference to FIG. 1, biological data may include, without limitation any result of any medical test, biological assessment, cognitive assessment, psychological assessment, or the like. System 100 may receive at least a biological data from one or more other devices after performance; system 100 may alternatively or additionally perform one or more assessments and/or tests to obtain at least a biological data, and/or one or more portions thereof, on system 100. For instance, at least biological data may include or more entries by a user in a form or similar graphical user interface 148 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, biological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a biological sample consistent with this disclosure.

With continued reference to FIG. 1, biological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or biological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and biological properties, behavior, and products of behavior. Behavioral phenotypes may include cognitive, personality, and behavior patterns. This may include effects on cellular and biological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-500. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter smithies'* and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosatetraenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of biological state data that may be used consistently with descriptions of systems and methods as provided in this disclosure.

With continued reference to FIG. 1, biological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Biological data may be obtained from a physically extracted sample. A physical sample may include a signal from a sensor configured to detect biological data of a user and record biological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmography equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, one or more user feature 108 may be stored in feature database 116. Feature database 116 may be implemented, without limitation, as a relational database, a key-value retrieval datastore such as a NO SQL database, or any other format or structure for use as a datastore that a person skilled in the art would recognize as suitable upon review of the entirety of this disclosure. Feature database 116 is described below in more detail.

With continued reference to FIG. 1, computing device 104 is configured to generate using element training data 120 a first machine-learning model. "Element training data" as used in this disclosure, is training data that contains a plurality of user features 108 and a plurality of correlated informed advisor elements. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, element training data 120 includes a plurality of user feature 108 and a plurality of correlated informed advisor elements. An "informed advisor element," as used in this disclosure, is a quality and/or or characteristic of an informed advisor. A quality and/or characteristic may include for example the education, specialty, area of expertise, conditions treated, beliefs, morals, and/or features practiced and/or displayed by informed advisors. Informed advisor may include, without limitation, a medical professional such as a doctor, nurse, nurse practitioner, functional medicine practitioner, pharmacist, physician assistant, and/or any professional with a career in medicine, nutrition, genetics, fitness, life sciences, spirituality, Christianity, insurance, and/or any other applicable industry. An informed advisor may include for example, a spiritual or philosophical advisor such as a religious leader, a pastor, imam, rabbi, a religious teacher, or the like. For example, an informed advisor may include a meditation teacher. In yet another non-limiting example, an informed advisor may include a yoga instructor, reiki coach, massage therapist, pastor, priest, life coach, spiritual coach, fitness coach, personal trainer, and the like. Informed advisor element 124 may include a description of one or more qualities, traits, and/or characteristics that an informed advisor may exhibit such as trustworthiness, supportive, kind, offers good advisor, positive influence, cooperative, humility, forgiveness, peacefulness, generous, faithfulness, and the like. Informed advisor elements may include a description of an informed advisor's education, training, credentials, specialties, and the like. For example, an advisor element may describe a massage therapist who holds an active massage therapy license, holds a degree from a massage therapy school, and who specializes in Swedish massage. In yet another non-limiting example, advisor element may describe a functional medicine doctor who obtained his medical degree from an ivy league medical school, performed his residency at a large hospital, is currently licensed as a medical doctor, completed training in functional medicine through the institute of functional medicine, and on average sees approximately 3000 patients each year. Informed advisor element 124 may include one or more elements specific to a particular informed advisor. For example, informed advisor element 124 relating to a cardiothoracic surgeon may include the surgeon's mortality rate, while informed advisor element 124 relating to a personal training may include the trainer's average weight loss among trainees who work with the trainer.

With continued reference to FIG. 1, computing device 104 is configured to locate an informed advisor within a specified geographical location. Computing device 104 may locate informed advisors using any network methodology as described herein. For example, computing device 104 may locate an informed advisor within a certain mile radius or distance as to where a user is located. In yet another non-limiting example, computing device 104 may locate an informed advisor within a specific state such as Texas or within a certain region such as New England. Computing device 104 retrieves an informed advisor element relating to an informed advisor located within a specified geographical location. In an embodiment, informed advisor element may be stored in a database such as advisory database 144 as described in more detail below. Computing device 104 updates element training data 120 utilizing a retrieved informed advisor element. In an embodiment, computing device 104 may update element training data 120 to reflect geographical and/or regional variances among correlations between user feature 108 and advisor elements. For instance and without limitation, a user feature 108 such as high testosterone may be commonly associated with an advisor element such as peacefulness for individuals residing in Southern states where manners are strictly enforced, whereas the same user feature 108 of high testosterone may be commonly associated with an advisor element such as forthcoming and directness for individuals residing in Northeast states. In yet another non-limiting example, a user feature 108 such as elevated fasting glucose may be commonly managed by informed advisors who are midlevel health practitioners such as nurse practitioners and physician assistants in one location of the country that is densely populated, whereas the same user feature 108 such as elevated fasting glucose may be commonly managed by a medical doctor in another location of the country where the population is minimally populated and house calls for medical appointments are frequently practiced.

With continued reference to FIG. 1, informed advisor element 124 may be self-reported, such as when an informed advisor may provide information about himself or herself. For example, an informed advisor such as a functional medicine doctor who believes she exhibits a patient and gentle bedside manner may self-report an informed advisor element 124 such as peacefulness and calm. In yet another non-limiting example, an informed advisor such as a yoga teacher who has had multiple extra-marital affairs may self-report an informed advisor element 124 such as sexual immorality. Informed advisors may self-report an informed advisor element 124 on a scale of how often they exhibit a certain quality. For example, a scale may include categories describing how often an informed advisor exhibits a quality such as a category of "never" when an informed advisor never exhibits a quality, a category such as "rarely" when an informed advisor may infrequently exhibit a quality, a category such as "sometimes" when an informed advisor may exhibit a quality more frequency, a category such as "frequently" when an informed advisor is repeatedly exhibiting a quality, and a category such as "always" when an informed advisor is consistently exhibiting a quality. Informed advisor element 124 may be reported about an informed advisor by an informed advisor's network which may include an informed advisor's family, friends, spouse, children, co-workers, acquaintances, and other users. For example, a student who routinely takes a yoga teacher's vinyasa yoga glass may generate and transmit to system 100 an advisor element that describes the yoga teacher as being kind, reliable, and loyal. In yet another non-limiting example, a patient of an informed advisor such as a gastroenterologist may generate an advisor element describing the patient's experience at a recent appointment with the gastroenterologist.

With continued reference to FIG. 1, a self-reported informed advisor element 124 may be received from a remote device 128 operated by an informed advisor. Remote device 128 may include without limitation, a display in communication with computing device 104, where a display may include any display as described herein. Remote device 128 may include an additional computing device, such as a mobile device, laptop, desktop, computer, and the like. Remote device 128 may transmit and/or receive one or more inputs from computing device 104 utilizing any network methodology as described herein. In an embodiment, an informed advisor such as a licensed acupuncturist may enter on her mobile device an advisor element that describes the acupuncturist as having high standards and exhibiting self-control and may transmit the informed advisor element 124 to computing device 104 utilizing any network methodology as described herein.

With continued reference to FIG. 1, computing device 104 is configured to generate a first machine-learning model using element training data and a first machine-learning algorithm. A machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, computing device 104 generates a first machine-learning model utilizing a first machine-learning algorithm that utilizes a user feature as an input and outputs advisor elements. First machine-learning model may include performing a series of one or more calculations, algorithms, and/or equations. First machine-learning algorithm includes any of the machine-learning algorithms as described above. Computing device 104 outputs using a user feature and a first machine-learning mode a plurality of advisor elements.

With continued reference to FIG. 1, computing device 104 may utilize machine-learning algorithms and models to identify a user feature 108. Computing device 104 may utilize physiological training data 136 in combination with a second machine-learning algorithm to generate a user feature 108. "Physiological training data," as used in this disclosure, is training data that contains a plurality of pairs of physiological data sets and user feature 108. "Physiological state data," as used in this disclosure, is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data may include any data suitable for use as a biological extraction 112 as described above. For instance and without limitation, physiological training data 136 may include physiological data that includes elevated dopamine levels and correlated user feature 108 that includes binge eating. In yet another non-limiting example, physiological training data 136 may include physiological data that includes low salivary estrogen levels and correlated user feature 108 that includes depressed mood and mood swings.

With continued reference to FIG. 1, computing device 104 generates using a second machine-learning algorithm and physiological training data 136 a feature model 140 correlating physiological data sets with user feature 108. "Feature model," as used in this disclosure, is any machine-learning model. A feature model 140 may include performing a series of one or more calculations, algorithms, and/or equations. A feature model 140 may be generated using one or more machine-learning algorithms. Machine-learning algorithms include any of the machine-learning algorithms as described above. Computing device 104 receives a biological extraction 112 from a user and identifies using the biological extraction 112 and a feature model 140 a user feature 108. For instance and without limitation, computing device 104 may utilize a biological extraction 112 from a user such as a user's urine neurotransmitter profile that contains elevated serotonin levels combination with physiological training set and a machine-learning algorithm to generate a feature model 140 that identifies a user feature 108 such as neuroticism.

With continued reference to FIG. 1, computing device 104 may generate a user feature 108 utilizing feature model and a machine-learning algorithm that includes a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, computing device 104 receives an informed advisor element 124 relating to an informed advisor. In an embodiment, computing device 104 may receive a self-reported informed advisor element from a remote device 128 as described above. In an embodiment, computing device 104 may receive an informed advisor element generated by users other than a subject informed advisor. Computing device 104 may locate a plurality of informed advisor element 124 generated by other users of system 100. In an embodiment, informed advisor element 124 may be stored in an advisory database 144. Advisory database 144 may be implemented as any data structure suitable for user as feature database 116 as described above in more detail. For instance and without limitation, an informed advisor such a pastor may have a plurality of informed advisor element 124 stored in an advisory database 144 generated by different members of the pastor's church, in addition to informed advisor element 124 generated by other individuals linked to the pastor's life such as neighbors, friends, family members, and the like. Computing device 104 may evaluate a plurality of informed advisor element 124. Evaluating a plurality of informed advisor element 124 may include performing one or more statistical calculations such as population mean, population standard deviation, population variance, and the like. For instance and without limitation, an informed advisor may have thirty seven informed advisor element 124 stored in advisory database 144. In such an instance, computing device 104 may aggregate thirty seven informed advisor element 124 and aggregate one or more informed advisor element 124 that contain similar content and input. For example, computing device 104 may aggregate informed advisor element 124 that confirm an advisor's credentials such if five of the thirty seven informed advisor element 124 contain confirmation that the informed advisor obtained a medical degree from a top medical school and completed a residency at a tertiary trauma center in a large city. In yet another non-limiting example, computing device 104 may evaluate informed advisor element 124 and perform calculations to determine how many of the informed advisor elements were generated by the informed advisor, how many were generated by family members and friends, and how many were generated by third-parties who may be a patient or customer of an informed advisor. Computing device 104 may evaluate informed advisor elements to determine how relevant and how new an informed advisor element may be. For instance and without limitation, an informed advisor element 124 may have been generated three years ago when an informed advisor didn't have a certain credential or experience teaching a particular form of yoga for example. In yet another non-limiting example, an informed advisor element may have been generated for the wrong informed advisor, such as if a user selects an informed advisor with the same name who is actually not the informed advisor the user knows and has a relationship with. For example, there may be twenty five John Smith's in the United States who are doctors and user may inadvertently select the wrong one. Evaluating a plurality of informed advisor element 124 may include evaluating who generated and transmitted an informed advisor element 124 and if the information contained within an informed advisor element 124 is accurate and truthful. For instance and without limitation, an informed advisor element 124 generated by an informed advisor's soon to be ex-spouse during a contentious divorce that labels the informed advisor as being jealous and an adulterer may be investigated if for example all other informed advisor element 124 relating to the informed advisor describe the informed advisor as being gentle, faithful, and exhibiting self-control. In yet another non-limiting example, an informed advisor element 124 that is generated by the informed advisor that portrays the informed advisor in a positive light while all other informed advisor elements contain negative traits and actions may be investigated. Investigations may include seeking additional informed advisor element 124 from close family members, friends, and colleagues of the informed advisor to determine if certain informed advisor element 124 contain outliers and may contain untruthful assertions. Investigations may include eliminating one or more informed advisor element 124 that are deemed to be untruthful or contain exaggerations or excessive puffery. Computing device 104 may select at least an informed advisor element from the plurality of informed advisor element 124 stored in advisory database 144 generated by other users. In an embodiment, informed advisor element 124 stored in advisory database 144 may be updated in real-time. One or more informed advisor elements stored in advisory database 144 may retrieved from websites that may rate and review informed advisors including for example HEALTHGRADES of Denver, Colorado, VITALS of Lyndhurst, New York, RATEMDS of Toronto, Canada, WEBMD of New York, New York, YELP of San Francisco, California, ZOCDOC of New York, New York, GOOGLE of Mountain View, California, FACEBOOK of Menlo Park, California, U.S. NEWS DOCTOR FINDER of New York, New York, CAREDASH of Cambridge, Massachusetts, and the like.

With continued reference to FIG. 1, receiving an informed advisor element 124 relating to an informed advisor may include a user selection of an informed advisor and receiving one or more informed advisor element 124 relating to the informed advisor from the advisory database 144. For instance and without limitation, a user may be recommended by a family member or friend to a particular informed advisor, and the user may select the informed advisor from a list displayed to the user such as on a graphical user interface 148. Graphical user interface 148 may include without limitation a form or other graphical element having data entry fields, where a user may select one or more fields to enter one or more informed advisors. Graphical user interface 148 may provide a drop-down menu and display one or more informed advisors where a user may select one or more informed advisors who may be located within a certain geographical distance in relation to the user. Graphical user interface 148 may list one or more categories of informed advisors, such as informed advisors who practice acupuncture, informed advisors who are functional medicine dermatologists, informed advisors who are yoga teachers and the like. Graphical user interface 148 may list one or more sub-categories of informed advisors such as if the informed advisor such as if a functional medicine gastroenterologist who specializes in specific diseases and conditions that include irritable bowel syndrome (IBS) and small intestinal bacterial overgrowth (SIBO).

With continued reference to FIG. 1, computing device 104 may receive an informed advisor element 124 relating to a user based on a user location. Computing device 104 may receive an element of user geolocation. An "element of user geolocation," as used in this disclosure, is an identification of a real-world geographical location of a user. An element of user geolocation 152 may be obtained from a radar source, remote device 128 such as a mobile phone, and/or internet connected device location. An element of user geolocation may include a global positioning system (GPS) of a user. An element of user geolocation may include geographic coordinates that may specify the latitude and longitude of a particular location where a user is located. Computing device 104 may utilize an element of user geolocation to located informed advisors located within the user geolocation. In an embodiment, a user may specify that the user only seeks to obtain informed advisors within a ten mile radius of the user. Computing device 104 retrieves an informed advisor element 124 from an informed advisor located within a user geolocation. For instance and without limitation, if a user's geolocation is specified as Plano, Texas, this may cause computing device 104 to retrieve an informed advisor element 124 for an informed advisor located in Fort Worth, Texas but not Oklahoma City, Oklahoma With continued reference to FIG. 1, computing device 104 may receive an element of informed advisor expertise 156. An "element of informed advisor expertise," as used in this disclosure, is any concentration and/or specialty that an informed advisor concentrates in and is considered to be an expert. A concentration may include a particular subject matter such as an area of medicine that a nurse practitioner may specialize in such as pediatric oncology. A concentration may include a particular form of yoga that a yoga teacher may instruct such as hatha yoga or vinyasa yoga. A specialty may include additional trainings and/or certifications that an informed advisor may hold and have achieve that may make the informed advisor an expert in a particular field or concentration. For example, a massage therapist be a specialist in Rolfing while a dietician may be an expert at working with clients who have autoimmune conditions such as rheumatoid arthritis, system lupus erythematosus, inflammatory bowel disease, and multiple sclerosis. In an embodiment, computing device 104 may generate an element of informed advisor expertise 156, such as to reflect a particular informed advisor and/or specialist that the user may be seeking. In yet another non-limiting example, an informed advisor such as user's primary care physician may recommend the user to seek a particular specialist such as if the primary care physician recommends that the user find a massage therapist because the user is currently undergoing treatment for chronic fatigue syndrome. Computing device 104 locates informed advisors who practice a specified expertise. For instance and without limitation, an element of informed advisor expertise 156 such as a request for an audiologist may cause computing device 104 to locate informed advisors who are practicing audiologists. In an embodiment, computing device 104 may filter practicing audiologists to retrieve one or more informed advisor element 124 who are audiologists and who meet other criteria specified by the user such as audiologists who are located within a certain geographical location of the user or who may be of a certain gender such as a user who seeks a male audiologist.

With continued reference to FIG. 1, computing device 104 determines using output advisor elements whether an informed advisor is compatible for a user. "Compatibility," as used in this disclosure, is a state where it is likely that an informed advisor and a user can work together with one another based on one or more shared commonalities or traits. Computing device 104 may determine that an informed advisor is compatible 160 with a user by utilizing output informed advisor elements generated from creating a first machine-learning model 132. Computing device 104 may compare output informed advisor elements generated using a first machine-learning model 132 to an informed advisor element received by computing device 104 that relates to an informed advisor. Computing device 104 may determine if any of the output informed advisor elements match the received informed advisor element relating to an informed advisor. Computing device 104 may evaluate output informed advisor elements to determine if they contain positive and/or negative characteristics and traits. For example, computing device 104 may determine that an informed advisor is not compatible 160 for a user if an output advisor element contains a description such as expressing excessive negativity and an informed advisor element relating to an informed advisor contains a description that the informed advisor has displayed negativity on occasion when treating some patients. In yet another non-limiting example, computing device 104 may determine that an informed advisor is compatible 160 for a user if an output informed advisor element contains a description such as being calm and not rushing and informed adios element relating to an informed advisor contains a description that the informed advisor is very patient.

With continued reference to FIG. 1, computing device 104 may display a plurality of elements such as on graphical user interface 148 as described above in more detail. "Elements," as used in this disclosure, are any qualities, characteristics, and/or features suitable for use as informed advisor elements. In an embodiment, computing device 104 may display as elements on graphical user interface 148 to a user a plurality of output advisor elements 164 generated by first machine-learning model 132. Computing device 104 may receive a user entry ranking 168 the plurality of output advisor elements 164. Ranking may include a numerical ranking such as a determination by a user as to output advisor elements that are most important to a user and which are least important. For instance and without limitation, a user may rank an element such as timeliness as being more important to the user than an element such as being patient. Computing device 104 may utilize a user entry ranking 168 a plurality of elements to determine in combination with output advisor elements 164 if an informed advisor is compatible for a user.

With continued reference to FIG. 1, computing device 104 may utilize a user entry ranking 168 a plurality of elements to determine if an informed advisor is compatible for a user by generating a loss function 172. Computing device 104 may utilize a loss function 172 analysis utilizing linear regression to determine if an informed advisor is compatible for a user. A "loss function," as used in this disclosure, is an expression of an output of which an optimization algorithm minimizes to generate an optimal result. As a non-limiting example, computing device 104 may calculate variables based on a user entry ranking 168 a plurality of elements, calculate an output of mathematical expression using the variables, and select an element that produces an output having the lowest size, according to a given definition of "size," of the sets of outputs representing each of the plurality of elements; size may, for instance, include absolute value, numerical size, or the like. Selection of different loss functions 172 may result in identification of different elements as generating minimal outputs; for instance, wherein element such as kindness is associated in a first loss function 172 with a large coefficient or weight, a user input such as honesty having a small coefficient or weight may minimize the first loss function 172, whereas a second loss function 172 where patience has a smaller coefficient but degree of variance from honesty may produce a minimal output for a different element having a larger coefficient for patience but more closely hewing to honesty.

With continued reference to FIG. 1, mathematical expression and/or loss function 172 may be generated using a machine learning to produce loss function 172: i.e., regression. Mathematical expression and/or loss function 172 be user-specific, using a training set composed of previous user rankings of elements; which may be updated continuously. Mathematical expression and/or loss function 172 may initially be seeded using one or more elements as described above. User may enter a new command changing mathematical expression, and then subsequent user selections may be used to generate a new training set to modify the new expression.

With continued reference to FIG. 1, mathematical expression and/or loss function 172 may be generated using machine learning using a multi-user training set. Training set may be created using data of a cohort of persons having similar demographic, religious, health, lifestyle characteristics, and/or element rankings to user. This may alternatively or additionally be used to seed a mathematical expression and/or loss function 172 for a user, which may be modified by further machine learning and/or regression using subsequent selection of elements. Computing device 104 minimizes a loss function 172 and determines whether an informed advisor is compatible for a user as a result of minimizing a loss function 172.

With continued reference to FIG. 1, computing device 104 may compare one or more user entry rankings to a mathematical expression representing an optimal combination of user entry rankings. Mathematical expression may include a linear combination of variables, weighted by coefficients representing relative importance of each variable in selecting an optimal user entry. For instance, a variable such as informed advisor timeliness may be multiplied by a first coefficient representing the importance of timeliness, a second variable such as informed advisor experience may be multiplied by a second coefficient representing the importance of experience, a third variable may be multiplied by a third coefficient representing the importance of that variable; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

With continued reference to FIG. 1, each user entry ranking of the plurality of user entry rankings may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each user input variable. A user entry ranking having a mathematical expression minimizing the error function may be selected, as representing an optimal expression of relative importance of variables to a system or user. In an embodiment, error function and loss function calculations may be combined; for instance, a user entry ranking resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to additional user entry rankings. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable containing a user entry ranking to the user. Sliders or other inputs may be initialized prior to user entry as equal or may be set to default values based on results of any machine-learning processes or combinations thereof as described in further detail below.

With continued reference to FIG. 1, computing device 104 is configured to generate a loss function utilizing a ranked plurality of elements and informed advisor elements, calculate a difference between the ranked plurality of elements and informed advisor elements as a function of minimizing the loss function, and determine whether an informed advisor is compatible for a user as a function of minimizing the loss function.

Figure 2:
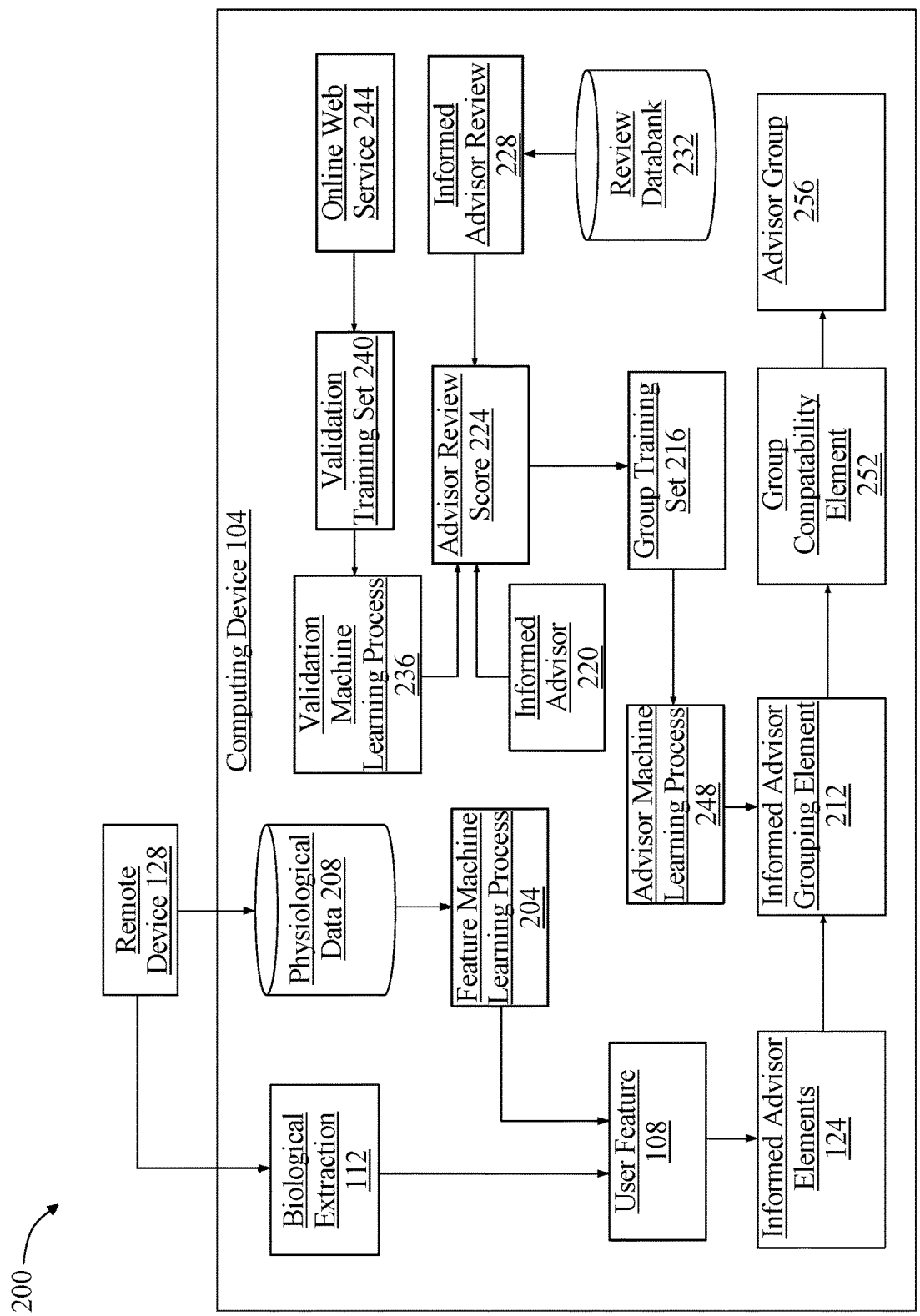
FIG. 2 is a block diagram illustrating an exemplary embodiment of a system for grouping informed advisor pairings

Referring now to FIG. 2, computing device 104 is configured to obtain user feature 108 using a feature machine-learning process 204. A "feature machine-learning process," as used in this disclosure, is a machine-learning process that uses physiological data 208 pertaining to a user as an input and outputs a user feature 108. As used in this disclosure "physiological data" includes any data suitable for use as physiological state data as described above in more detail in reference to FIG. 1. Physiological data includes the direct or indirect observation of variables attributable to normative functioning of systems and subsystems in the user. Variables may include, without limitation, measurable properties and functions of the biological systems and subsystems, such as heart rate, blood pressure, cortical activity, biochemical markers, and the like thereof. Remote device 128 may collect information pertaining to a user input containing physiological data 208 in various ways such as, without limitation, a self-report by the user, a third party input acting on behalf of a user, including without limitation, a family member, friend, or acquaintance, and the like. In yet another non-limiting example, physiological data 208 may be identified and/or collected as a function of a survey or questionnaire. Additionally or alternatively the user feature 108 may be obtained as a function of biological extraction 112 pertaining to the user, wherein biological extraction is further described above in FIG. 1. Information pertaining to a user biological extraction may be collected based on one or more inputs and/or results received from a remote device 128 operated by a user, as described above in more detail in reference to FIG. 1. Computing device 104 may receive an input containing a biological extraction and/or information relating to a biological extraction using any network methodology as described herein.

Still referring to FIG. 2, computing device 104 is configured to receive an informed advisor element 124 as described above. In an embodiment, informed advisor element 124 may include a quality and/or characteristic such as the experience, morals, specialization, education, beliefs, and/or features practiced and/or displayed by informed advisors. Computing device 104 may receive informed advisor element as a function of remote device 128, wherein informed advisor element 124 input may be generated as a function of a self-report from the informed advisor, as a function of user input, or as a function of surveys and/or questionnaires.

With continued reference to FIG. 2, computing device 104 is configured to generate an informed advisor grouping element 212 as a function of the informed advisor element 124. As used in this disclosure, "Informed advisor grouping element", are qualities or characteristics such as, without limitation, expertise, reviews, and user compatibility. For example, a quality, trait, or characteristic, may be comprised of as trustworthiness, supportive, kind, offers good advisor, positive influence, cooperative, humility, forgiveness, peacefulness, generous, faithfulness, and the like thereof. Additionally or alternatively, informed advisor grouping element rate be comprised of a quality, trait, or characteristic such as, without limitation, expertise, field of study, academic qualifications, certifications, academic studies, work experience, client interactions, previous client reviews, and the like thereof.

Still referring to FIG. 2, computing device is further configured to receive a grouping training set 216. A "grouping training set," as used in this disclosure, is training data relates an informed advisor 220 to an advisor review score 224. As used in this disclosure, an informed advisor 220 may consist of, without limitation, a medical professional such as a doctor, nurse, nurse practitioner, functional medicine practitioner, pharmacist, physician assistant, and/or any professional with a career in medicine, nutrition, genetics, fitness, life sciences, spirituality, religion, insurance, and/or any other applicable industry. Informed advisor 220 may include for example, a spiritual or philosophical advisor such as a religious leader, a pastor, imam, rabbi, a religious teacher, or the like. For example, informed advisor 220 may include a meditation teacher. In yet another non-limiting example, an informed advisor may include a yoga instructor, reiki coach, massage therapist, pastor, priest, life coach, spiritual coach, fitness coach, personal trainer, and the like. An "advisor review score", as used in this disclosure, is a data including any numerical, character, and/or symbolic data that reflects a score indicating one or more traits, qualities, and/or characteristics that an informed advisor may or may not exhibit. Advisor review score 224 relates reviews of informed advisor 220 to informed advisor grouping element 212 and generates a quantitative value of each quality, trait, and/or characteristic.

Still referring to FIG. 2, computing device 104 is configured to receive an informed advisor review from a review databank. An "informed advisor review", as used in this disclosure, consists of any comment, remark, note, statement, analysis, evaluation, assessment, appraisal, examination, scrutiny, inquiry, probe, inspection, study, audit and the like thereof relating the informed advisor to a previous client opinion, belief, experience, or knowledge. For example, an informed advisor review may consist of a user survey analyzing the informed advisor based on a previous experience with the informed advisor. Informed advisor review 228 may be received from a review databank 232, wherein review databank 232 may be any storage, culmination, collection, depository, or memory cache. For example, a review databank may include, without limitation, Google My Business, Facebook, Yelp, Zocdoc, BBB, Yellowpages, Manta, Angie's List, RateMDs, WebMD, Thumbtack, Healthgrades, Vitals, or Wellness.com.

Still referring to FIG. 2, computing device 104 is configured to determine the validity of an informed advisor review, using a validation machine-learning process 236. A "validation machine-learning process", as used in this disclosure, consists of any supervised, unsupervised, or reinforcement machine-learning process that computing system 104 may or may not use in the determination of the validity of an informed advisor review. Validation machine-learning process 236 may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbours, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG). Validation machine learning process 236 may be generated as a function of a validation training set 240. A "validation training set", as used in this disclosure relates a review indicator to an authenticity score of a review. For example, a review indicator may be, without limitation, common spam or review indicator word and/or phrase such as "act now", "apply now", "buy now", "click below", "click here", "click me to download", "click this link", "click to remove", "call free", "call now", "claim now", "contact us immediately", "get now", "sign up free", "show now", "order now", "get paid", "ad", "amazing", "bargain", "beneficial order", "cheap", "clearance", "congratulations", "direct marketing", "don't delete", "email marketing", "fantastic", "free", "free trial", "gift certificate", "offer expires", "offer extended", "online marketing", "opportunity", "opt in", "promise you", "sale", "spam", "this isn't junk", "top urgent", "visit our website", and the like thereof. Additionally or alternatively, an "authenticity score", as used in this disclosure, is any data including any numerical, character, and/or symbolic data that reflects the likelihood for a review to be valid or invalid. For example, a review may state the words "this isn't spam", which may lower the authenticity score below a set threshold limit and signify the review has a high likelihood for being invalid or fake. Validation training set 240 may be obtained from data from an online webservice 244. Online webservice 244 may be any URL or website that stores or otherwise depicts specific spam words associated within reviews. For example, and without limitation, an online webservice such as automational.com and codemedy.com may indicate the word and/or phrase "free investment", which would then be an indicator that computing system 200 may utilize to generate the review score as a function of the informed advisor review.

Still referring to FIG. 2, an advisor machine learning process 248 is used to compute the informed advisor grouping element 212 as a function of grouping training set 216. An "advisor machine-learning process", as used in this disclosure, consists of any supervised, unsupervised, or reinforcement machine-learning process that computing system 104 may or may not use in the computation of the informed advisor grouping element, wherein grouping training set 216 is an input and informed advisor grouping element 212 is the output. For example advisor machine learning process 248 may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve Bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG). A "grouping training set", as used in this disclosure relates a first quality, trait, and/or characteristic to a second quality, trait, or characteristic, which then is related to a plurality of qualities, traits, and/or characteristics that have symbiotic functions. For example, a characteristic of kind may relate to the characteristic of humble, while a characteristic of angry may relate to the characteristic of mean.

Still referring to FIG. 2, determine a group compatible element 252 as a function of informed advisor grouping element 212. A "group compatible element", as used in this disclosure, comprises any pairing, similarity, likeness, sameness, equivalence, uniformity, relatedness, or the like thereof of qualities, traits, and/or characteristics that two informed advisors have in common. Group compatible element 252 may consist of an informed advisor group that may share one or more informed advisor grouping elements 212. Group compatible element 252 may identify the compatibility of a first informed advisor in relation to a second informed advisor. For example, a first advisor may have qualities, traits, and/or characteristics associated with trustworthiness, supportive and, faithfulness, which are similar to a second advisor. The first and second advisor may then be grouped together in a similar group compatible element. For example, a first advisor may have qualities, traits, and/or characteristics associated with trustworthiness, supportive and, faithfulness, while a second advisor has qualities, traits, and/or characteristics associated with rude, negative influence, and negative reinforcement. In this example, the first and second advisors may not share similar qualities, traits, and/or characteristics and may not be grouped in a similar group compatible element.

Still referring to FIG. 2, computing device 104 groups informed advisors of a plurality of advisors in an advisor group 256 as a function of the group compatible element to enhance the user feature. An "advisor group" as used in this disclosure, is one or more informed advisors of a plurality of expertise areas, that share similar group compatible elements, wherein the user may benefit from the one or more informed advisors. Advisor group 256 may consist of one or more informed advisors to enhance a user feature. For example, advisor group 256 may consist of, without limitation, a nutritionist, a cardiologist, a fitness coach, a life coach, and a primary care physician for a user feature associated with obesity. For example, advisor group 256 may consist, without limitation, a yoga instructor, a lifestyle coach, a religious leader, and a therapist for a user feature associated with anxiety and/or depression.

Still referring to FIG. 2, group, computing device 104 is configured to determine the group compatible element comprises displaying on the computing device a plurality of elements describing an informed advisor group quality. Computing device 104 receives a user entry ranking the plurality of elements and selects an informed advisor group as a function of the ranked plurality of elements. Further details are discussed above in FIG. 1. The informed advisor group is selected by generating a loss function utilizing the ranked plurality of elements and the informed advisor group qualities, calculating a difference between the ranked plurality of elements and the informed advisor group qualities as a function of minimizing the loss function, and determining an informed advisor group compatibility for the user as a function of calculating the difference. This may be performed using any of the methodologies as described above in more detail in reference to FIG. 1.

Figure 3:
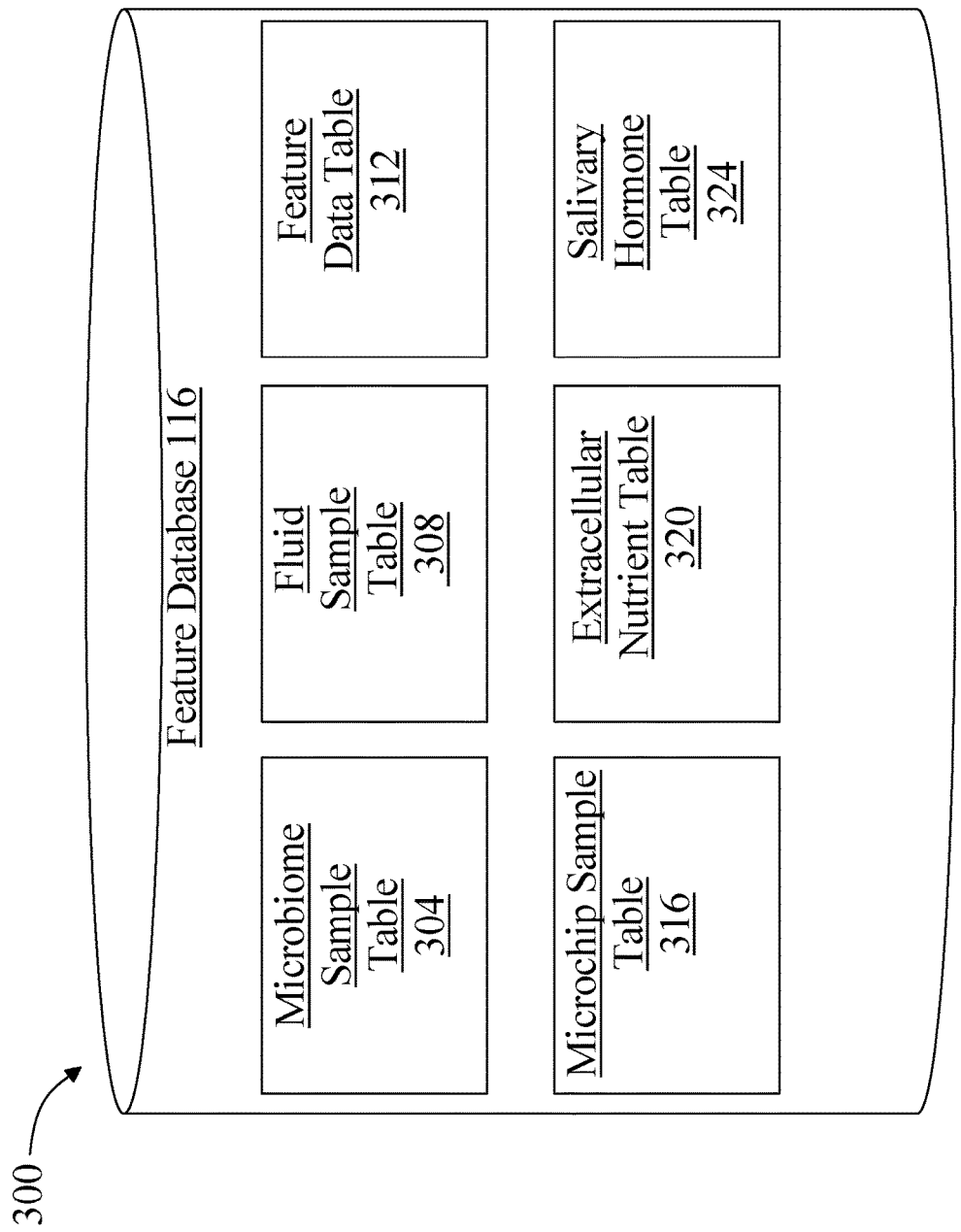
FIG. 3 is a block diagram illustrating an exemplary embodiment of a feature database.

Referring now to FIG. 3, an exemplary embodiment of a feature database 116 is illustrated. Feature database 116 may be implemented as any data structure as described above. One or more tables contained within feature database 116 may include microbiome sample table 304 may include one or more biological extraction 112 relating to the microbiome. For instance and without limitation, microbiome sample table 304 may include a physically extracted sample such as a stool sample analyzed for the presence of pathogenic species such as parasites and anaerobes. One or more tables contained within feature database 116 may include fluid sample table 308; fluid sample table 308 may include one or more biological extraction 112 containing fluid samples. For instance and without limitation, fluid sample table 308 may include a urine sample analyzed for the presence or absence of glucose. One or more tables contained within feature database 116 may include feature data table 312; feature data table 312 may include one or more user feature 108. For instance and without limitation, feature data table 312 may include a unique genetic marker such as a mutated SLCO1B2 gene associated with high levels of blood fatty acids. One or more tables contained within feature database 116 may include microchip sample table 316; microchip sample table 316 may include one or more biological extraction 112 obtained from a microchip. For instance and without limitation, microchip sample table 316 may include an intracellular nutrient level obtained from a microchip embedded under a user's skin. One or more tables contained within feature database 116 may include extracellular nutrient table 320; extracellular nutrient table 320 may include one or more biological extraction 112 containing extracellular nutrient levels. For instance and without limitation, extracellular nutrient table 320 may include an extracellular level of potassium. One or more tables contained within feature database 116 may include salivary hormone table 24; salivary hormone table 324 may include one or more biological extraction 112 containing salivary hormone levels. For instance and without limitation, salivary hormone table 324 may include a measurement of a user's salivary estradiol, estrone, progesterone, and testosterone levels.

Figure 4:
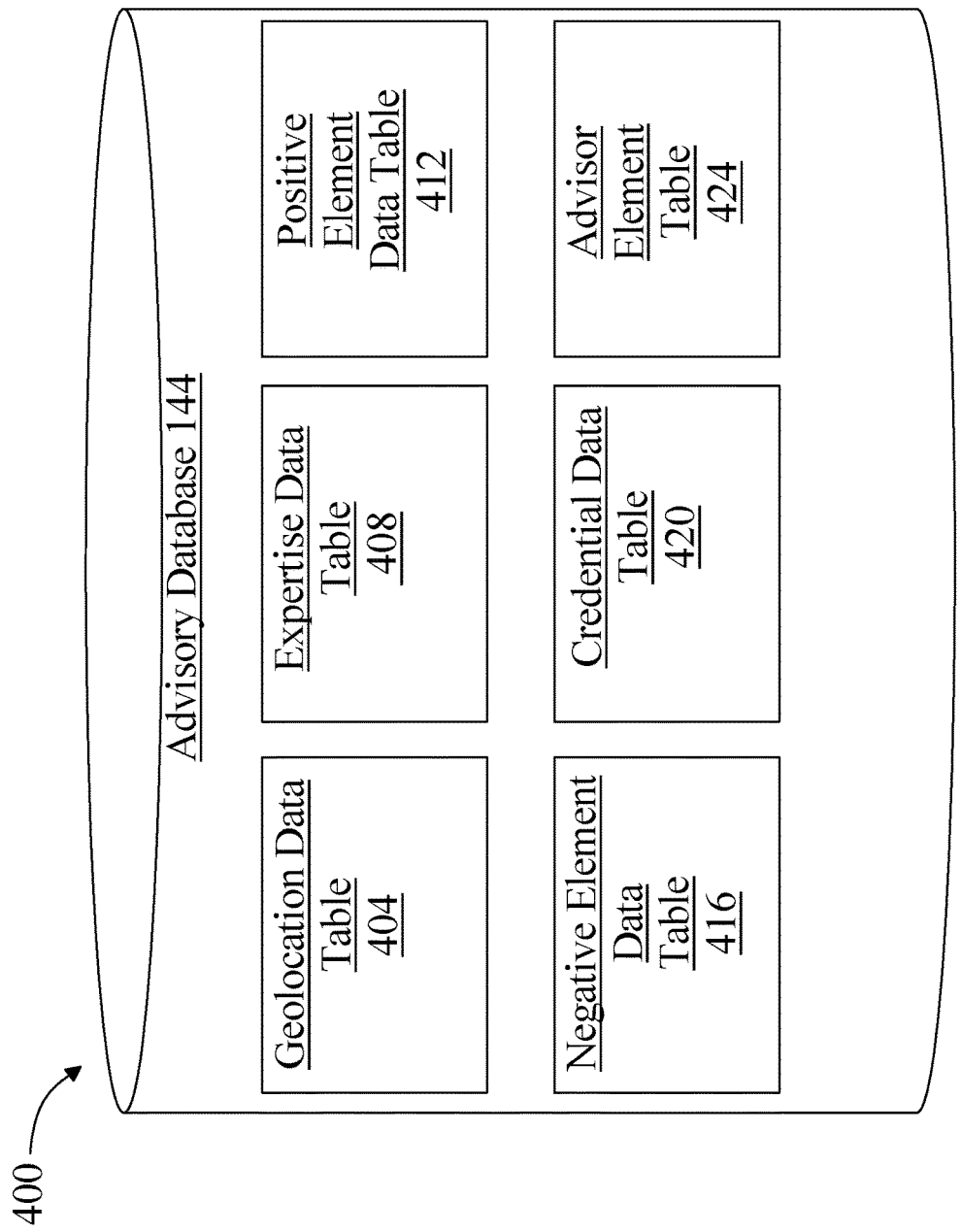
FIG. 4 is a block diagram illustrating an exemplary embodiment of an advisory database.

Referring now to FIG. 4, an exemplary embodiment of advisory database 144 is illustrated. Advisory database 144 may be implemented as any data structure as described above in more detail. One or more tables contained within advisory database 144 may include geolocation data table 404; geolocation data table 404 may include one or elements of geolocation data. One or more tables contained within advisory database 144 may include expertise data table 408; expertise data table 408 may include one or more elements of expertise data. One or more tables contained within advisory database 144 may include positive element data table 412; positive element data table 412 may include one or more positive informed advisor elements such as trustworthiness, positive influence, humility, calm bedside manner, and the like. One or more tables contained within advisory database 144 may include negative element data table 416; negative element data table 416 may include one or more negative informed advisor elements such as hatred, jealousy, temper tantrums, manipulation, and gossiping. One or more tables contained within advisory database 144 may include credential data table 420; credential data table 420 may include one or more elements of credential data. One or more tables contained within advisory database 144 may include advisor element table 424; advisor element table 424 may include one or more advisor elements.

Figure 5:
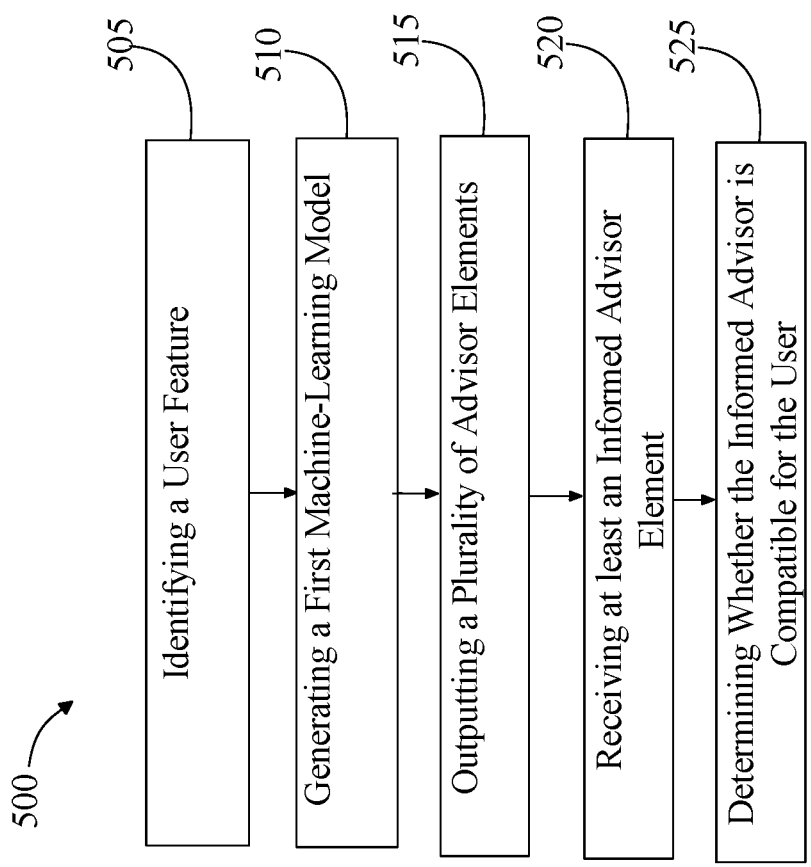
FIG. 5 is a process flow diagram illustrating an exemplary embodiment of a method of customizing informed advisor selection.

Referring now to FIG. 5, an exemplary embodiment of a method 500 of customizing informed advisor pairings is illustrated. At step 505, a computing device 104 identifies a user feature 108 wherein a user feature 108 contains a biological extraction 112. User feature 108 includes any of the user feature 108 as described above in reference to FIGS. 1-3. For instance and without limitation, a user feature 108 may include a trait that the user exhibits such as joy and being glad not based on circumstances. In yet another non-limiting example, a user feature 108 may include a quality such self-control, where a user restraint his or her emotions, actions, and desires. In yet another non-limiting example, a user feature 108 may include a biological extraction 112 such as a stool test analyzed for parasites, bacteria and yeast cultures, and markers of inflammation. In an embodiment, a biological extraction 112 may be contained within feature database 116.

With continued reference to FIG. 5, computing device 104 may identify a user feature 108 using one or more machine-learning models. Computing device 104 may generate using a machine-learning algorithm and physiological training data 136 a feature model 140 correlating physiological data sets with user feature 108. Physiological training data 136 includes any of the physiological training data 136 as described above in reference to FIGS. 1-3. Physiological data includes any of the physiological data as described above in reference to FIGS. 1-3. Computing device 104 may generate a machine-learning algorithm which includes any of the machine-learning algorithms as described herein. For instance and without limitation, machine-learning algorithm may include a supervised machine-learning algorithm or an unsupervised machine-learning algorithm. Machine-learning algorithm may include a classification algorithm, such as for example naïve Bayes, k-nearest neighbor, decision tree, and/or random forest. Classification algorithms include any of the classification algorithms as described above in reference to FIGS. 1-3. Computing device 104 receives a biological extraction 112 from a user. Biological extraction 112 includes any of the biological extraction 112 as described above in reference to FIGS. 1-3. Computing device 104 uses a biological extraction 112 from a user and feature model 140 to identify the user feature 108.

With continued reference to FIG. 5, computing device 104 generates a first machine-learning model using element training data 120. A first machine-learning model includes any of the machine-learning models as described above in reference to FIGS. 1-3. Element training data 120 includes a plurality of user feature 108 and a plurality of correlated advisor elements as described above in more detail in reference to FIGS. 1-3. Computing device 104 generates first machine-learning algorithm that utilizes a user feature 108 as an input and outputs advisor elements utilizing element training data. Element training data 120 may be continuously updated and may be updated based on geographical location. Computing device 104 may locate an informed advisor within a specific geographical location. For example, computing device 104 may locate an informed advisor who may be within a certain distance of user as described above in more detail in reference to FIG. 1. Computing device 104 may retrieve at least an informed advisor element relating to a located informed advisor. In an embodiment, computing device 104 may retrieve at least an informed advisor element from advisory database 144. Computing device 104 updates element training data 120 utilizing a retrieved informed advisor element. In an embodiment, updating may include incorporating a retrieved informed advisor element into element training data 120 such as for example, as a data element.

With continued reference to FIG. 5, at step 515, computing device 104 outputs using a user feature and a first machine-learning model a plurality of advisor elements. Output advisor elements 160 may include advisor elements that are compatible with a user. Output advisor elements may include both positive and negative advisor elements. For instance and without limitation, a first machine-learning model 132 may determine that a user is able to tolerate informed advisors who may exhibit neurotic tendencies, but a user is not able to tolerate informed advisors who are overly sensitive. In yet another non-limiting example, a first machine-learning model 132 may determine that a user is best suited to be seen by a functional medicine doctor and not a massage therapist for a dislocated shoulder joint. First machine-learning model 132 may be created utilizing any of the methods as described above in reference to FIGS. 1-4.

With continued reference to FIG. 5, at step 520, computing device 104 receives at least an informed advisor element relating to an informed advisor. An informed advisor element includes any of the informed advisor elements as described above in reference to FIGS. 1-3. For instance and without limitation, informed advisor element may include qualities, characteristics, education, specialty, area of expertise, and/or conditions treated by an informed advisor. For example, an informed advisor element may describe one or more conditions or types of patients that an informed advisor works with, such as a massage therapist who specializes in working with clients who have been injured in motor vehicle accidents. In yet another non-limiting example, an informed advisor element may describe the education and credentials of an informed advisor, such as a doctor of osteopathy who is board certified in genetics. An informed advisor element may include a review of an informed advisor, such as from a patient or client of an informed advisor. Computing device 104 may receive from a remote device 128 operated by an informed advisor a self-reported informed advisor element. For example, an informed advisor such as a chiropractor may self-report that he specializes in diagnosing and treating conditions that include back pain, chronic pain, herniated disc, migraine headache, neck pain, and sciatica. In an embodiment, an informed advisor element may be generated by a third-party such as a friend, family member, acquittance, co-worker, of the informed advisor. For example, a client of the informed advisor may generate an informed advisor element that describes the informed advisor as having a positive bedside manner and being on time for appointments.

With continued reference to FIG. 5, computing device 104 may locate a plurality of informed advisor elements generated by other users such as on other third-party websites as described above in more detail. For example, computing device 104 may extract one or more informed advisor elements that may be placed on a website such as Yelp.com or Zocdoc.com. Computing device 104 evaluates a plurality of informed advisor elements. Computing device 104 may evaluate a plurality of informed advisor elements to determine if an informed advisor element has been generated under false pretenses or if an informed advisor element contains inaccurate information as described above in more detail in reference to FIG. 1. Evaluating may include performing one or more calculations or statistical analyses on informed advisor elements to determine commonalities among a plurality of informed advisor elements. For example, computing device 104 may seek to determine how many informed advisor elements contain positive remarks and qualities and how many informed advisor elements contain negative remarks and qualities. Computing device 104 may select an informed advisor element from a plurality of informed advisor elements generated by other users.

With continued reference to FIG. 5, computing device 104 may receive an informed advisor element based on a user geolocation. Computing device 104 may receive an element of user geolocation data 152. Geolocation data includes any of the geolocation data as described above. For example, an element of user geolocation data 152 may specify the longitude and latitude of where a user is precisely located. Computing device 104 may locate informed advisors located within the user geolocation. For instance and without limitation, an element of user geolocation data 152 that determines the user is located in New Orleans, Louisiana may cause computing device 104 to located informed advisors who may be located in New Orleans, Metairie, Covington, Akers, and Laplace. Computing device 104 retrieves at least an informed advisor element from an informed advisor located within the user geolocation.

With continued reference to FIG. 5, computing device 104 may receive an informed advisor element based on an informed advisor area of expertise. Computing device 104 may receive an element of informed advisor expertise, that may be entered from remote device 128 and/or stored in advisory database 144. Computing device 104 locates informed advisors who engage in and practice the area of expertise. For instance and without limitation, computing device 104 may locate an informed advisor who is an expert at a particular specialty such as Reiki massage. In yet another non-limiting example, computing device 104 may locate an informed advisor who is an expert at treating a particular condition or diagnosis such as an expert at Lyme disease or an expert at irritable bowel syndrome. Computing device 104 retrieves an informed advisor element from an informed advisor who engages and/or practices a particular specialty or expertise.

With continued refence to FIG. 5, at step 525, computing device 104 determines using output advisor elements whether an informed advisor is compatible for a user. Computing device 104 may determine whether an informed advisor is compatible by comparing output advisor elements to an informed advisor element received that relates to an informed advisor to determine if they may match or contain similar entries. For example, computing device 104 may determine that an informed advisor is compatible for a user if an output advisor element contains truthfulness and an informed advisor element relating to an informed advisor contains honesty. Computing device 104 may determine that an informed advisor is compatible for a user by displaying on a computing device, a plurality of elements. Elements include any of the elements as described above in reference to FIG. 1. Computing device 104 may display elements on graphical user interface 148. Computing device 104 receives a user entry ranking 168 a plurality of elements. Computing device 104 selects an informed advisor utilizing ranked elements generated by a user. For instance and without limitation, computing device 104 may select an informed advisor who holds a medical degree from an ivy league school if a user ranks educational background higher than an element such as accuracy of diagnosis.

With continued reference to FIG. 5, computing device 104 may select an informed advisor utilizing a loss function 172. Computing device 104 generates a loss function 172 utilizing ranked plurality of elements as variables and informed advisor elements. Computing device 104 may assigned a weighted variable score to a ranked element. Computing device 104 may minimize the loss function 172 utilizing any of the methodologies as described above in reference to FIGS. 1-3. Computing device 104 generates a loss function utilizing ranked plurality of elements and informed advisor elements to calculate a difference between the ranked plurality of elements and informed advisor elements as a function of minimizing the loss function. Computing device 104 determines whether an informed advisor is compatible for a user as a function of minimizing a loss function 172.

Figure 6:
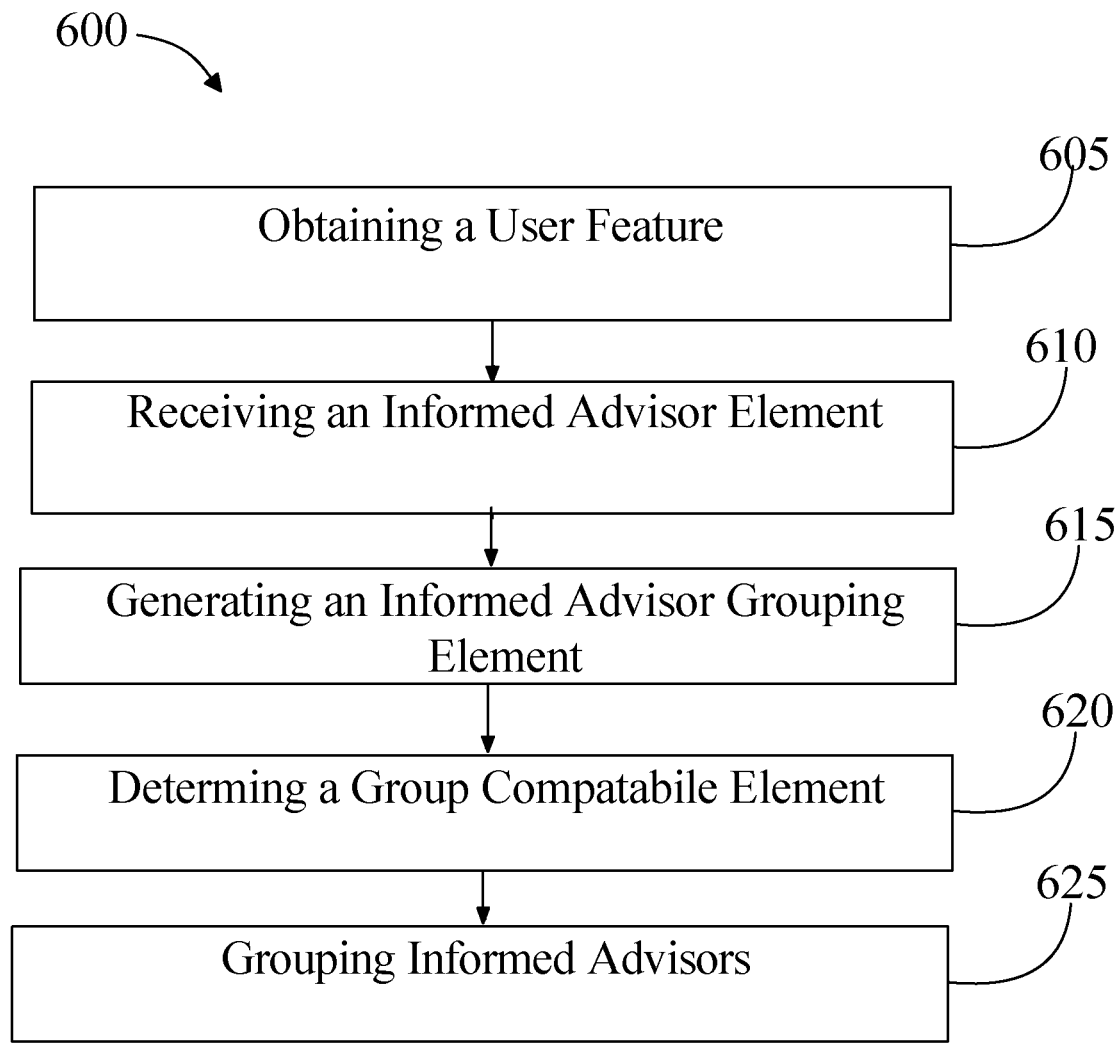
FIG. 6 is a process flow diagram illustrating an exemplary embodiment of a method of grouping informed advisor selection.

Referring now to FIG. 6, an exemplary embodiment of a method 600 of grouping informed advisor pairings is illustrated. At step 605, a computing device 104 obtains a user feature 108. User feature 108 includes any of the user feature 108 as described above in reference to FIGS. 1-5. For instance, and without limitation, a user feature 108 may include a trait that the user exhibits such as joy and being glad not based on circumstances. In yet another non-limiting example, a user feature 108 may include a quality such self-control, where a user restraint his or her emotions, actions, and desires. In yet another non-limiting example, a user feature 108 may include a biological extraction 112 such as a stool test analyzed for parasites, bacteria and yeast cultures, and markers of inflammation. In an embodiment, a biological extraction 112 may be contained within feature database 116.

With continued reference to FIG. 6, computing device 104 may identify a user feature 108 using one or more machine-learning models. Computing device 104 may generate using a feature machine-learning process 204 and physiological data 208 correlating physiological data sets with user feature 108. Physiological data 208 includes any of the physiological training data 208 as described above in reference to FIGS. 1-5. Physiological data includes any of the physiological data as described above in reference to FIGS. 1-5. Computing device 104 may generate a feature machine-learning process which includes any of the machine-learning processes as described herein. For instance, and without limitation, feature machine-learning process may include a supervised machine-learning process or an unsupervised machine-learning process. Feature machine-learning process may include a classification process, such as for example naïve Bayes, k-nearest neighbor, decision tree, and/or random forest. Classification processes include any of the classification processes as described above in reference to FIGS. 1-5. Computing device 104 receives a biological extraction 112 from a user. Biological extraction 112 includes any of the biological extraction 112 as described above in reference to FIGS. 1-5. Computing device 104 uses a biological extraction 112 from a user and feature machine learning process 204 to identify the user feature 108.

With continued reference to FIG. 6, at step 610, computing device 104 receives at least an informed advisor element relating to an informed advisor as discussed in detail in FIG. 5. An informed advisor element includes any of the informed advisor elements as described above in reference to FIGS. 1-5. For instance, and without limitation, informed advisor element may include qualities, characteristics, education, specialty, area of expertise, and/or conditions treated by an informed advisor. Computing device 104 may receive informed advisor elements 124 as a function of an informed advisor a self-reported informed advisor element.

With continued reference to FIG. 6, at step 615, computing device 104 generates an informed advisor grouping element as a function of the informed advisor element. Computing device 104 may generate informed advisor grouping element 212 as a function of qualities or characteristics such as, without limitation, expertise, reviews, and user compatibility. Computing device 104 may generate informed advisor grouping element as a function of a quality, trait, or characteristic such as, without limitation, expertise, field of study, academic qualifications, certifications, academic studies, work experience, client interactions, previous client reviews, and the like thereof.

Still referring to FIG. 6, computing device 104, generates informed advisor grouping element 212 by receiving a grouping training set 216 relating an informed advisor to an advisor score review. Computing device 104 may receive a grouping training set 216 that relates an informed advisor 220 to an advisor review score 224, wherein grouping training set 216 is described above in reference to FIGS. 1-5. For example, a priest may have a high advisor review score for being kind, thoughtful, and wise based on previous reviews from other clients. For instance, a medical professional, a yoga instructor, and a life coach are all examples of an informed advisor, wherein advisor review score 224 is described above in reference to FIGS. 1-5. For instance, a quantitative value of five for trustworthiness may be generated as a result of the reviews associated with that informed advisor.

Still referring to FIG. 6, computing device 104, receives an informed advisor review 228 from a review databank 232, wherein informed advisor review is described above in reference to FIGS. 1-5. For example, an informed advisor review 228 may consist of a user survey analyzing the informed advisor based on a previous experience with the informed advisor, wherein review databank 232 is described above in reference to FIGS. 1-5. For instance, computing device 104 may receive a review stating an informed advisor was blunt from Yelp. Computing device 104 determines the validity of the review using a validation machine-learning process 236 as a function of a validation training set 240. Validation machine-learning process 236 may encompass any supervise, unsupervised or reinforcement machine learning processes to validate the authenticity of the review. Validation training set 240 is be generated as a function of computing device 104 obtaining data from an online webservice 244. Computing device 104 generates the advisor review score 224 as a function of the informed advisor review 228. For instance, computing device 104 may indicate a review to be invalid when the phrase "free investment" is directly stated in the review. Computing device 104, generates informed advisor grouping element 212 using an advisor machine learning process 248, wherein advisor machine learning process utilizes grouping training set 216 to compute informed advisor grouping element 212, wherein informed advisor grouping element 212 is described above in reference to FIGS. 1-5. Computing device 104 utilizes advisor machine learning process 248 by inputting grouping training set 216 and outputting informed advisor grouping element 212.

Still referring to FIG. 6, at step 620, computing device 104 determines a group compatible element 252 as a function of informed advisor grouping element 212. Computing device 104 determines advisor qualities, traits, and/or characteristics, and groups informed advisors according to the plurality of qualities, traits and/or characteristics. For example, a first advisor may have qualities, traits, and/or characteristics associated with trustworthiness, supportive and, faithfulness, which are similar to a second advisor. The first and second advisor may then be grouped together in a similar group compatible element.

Still referring to FIG. 6, at step 625, computing device 104 groups informed advisors of a plurality of informed advisors in an advisor group 256. Computing device 104 groups the informed advisors as a function of group compatible element 252 to enhance the user feature. For example, computing device, 104 may group a nutritionist, a cardiologist, a fitness coach, a life coach, and a primary care physician in an advisor group for a user feature associated with obesity. Additionally or alternatively, computing device 104 may group a yoga instructor, a lifestyle coach, a religious leader, and a therapist in an advisor group for a user feature associated with anxiety and/or depression.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
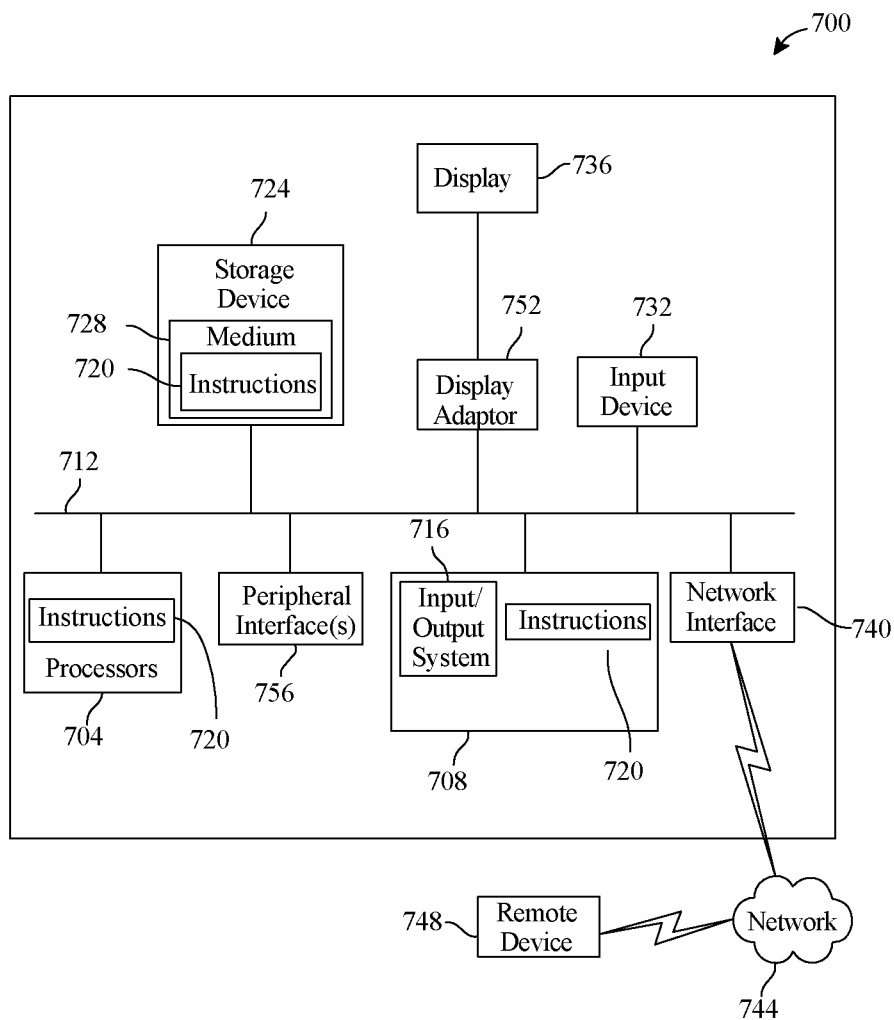
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote device 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for grouping informed ad visor pairings, the system comprising:
   a computing device, the computing device configured to:
   obtain a user feature of a user, wherein obtaining the feature comprises generating a feature model iteratively trained with physiological training data comprising a plurality of physiological data sets correlated to a plurality of user features, wherein the feature model is configured to receive a biological extraction comprising user physiological data related to at least genomic data of the user, perform a classification algorithm, and output the user feature;
   receive an informed ad visor element relating an informed ad visor to the user feature, wherein receiving an informed advisor element comprises training, using element training data comprising a plurality of user features and a plurality of correlated informed advisor elements, a machine-learning model configured to receive the user feature as an input and output the informed advisor element, wherein the computing device is configured to iteratively update the element training data to reflect geographical variances among correlations between the plurality of user features and advisor elements;

generate an informed advisor grouping element as a function of the informed advisor element, wherein generating further comprises:

receiving a grouping training set, the grouping training set relating an informed advisor to an advisor review score; and calculating the informed advisor grouping element as a function of the grouping training set using an advisor machine-learning process, the advisor machine-learning process trained using the grouping training set;

determine, as a function of the informed advisor grouping element, a group compatible element;

group, an informed advisor of a plurality of informed advisors as a function of the group compatible element, the group compatible element configured to enhance the user feature; and display the group compatible element on a graphical user interface.

2. The system of claim 1, wherein receiving the informed advisor element further comprises:

receiving an element of informed advisor expertise;

locating an informed advisor who engages the expertise; and retrieving the informed advisor element as a function of locating the informed advisor who engages the expertise.

3. The system of claim 1, wherein the advisor review score further comprises:

receiving an informed advisor review from a review databank;

determining, using a validation machine-learning process, the validity of the review as a function of a validation training set, wherein the validation training set relates a review indicator to an authenticity score of a review; and generating the advisor review score as a function of the informed advisor review.

4. The system of claim 3, wherein the review databank comprises a review platform containing a user generated review.

5. The system of claim 3, wherein the validation training set is retrieved from an online web service.

6. The system of claim 3, wherein the authenticity score consists of a likelihood for a review to be validated.

7. The system of claim 1, wherein the group compatible element identifies the compatibility of a first informed advisor in relation to a second informed advisor.

8. The system of claim 1, wherein determining the group compatible element further comprises:

displaying on the computing device a plurality of elements describing an informed advisor group quality;

receiving a user entry ranking the plurality of elements; and selecting an informed advisor group quality as a function of the ranked plurality of elements.

9. The system of claim 8, wherein selecting the informed advisor group quality further comprises:

generating a loss function utilizing the ranked plurality of elements and the selected informed advisor group quality;

calculating a difference between the ranked plurality of elements and the selected informed advisor group quality as a function of minimizing the loss function; and determining an informed advisor group compatibility for the user as a function of calculating the difference.

10. A method of grouping informed ad visor pairings, the method comprising:

obtaining, by a computing device, a user feature, wherein obtaining the feature comprises generating a feature model iteratively trained with physiological training data comprising a plurality of physiological data sets correlated to a plurality of user features, wherein the feature model is configured to receive a biological extraction comprising user physiological data related to at least genomic data of the user, perform a classification algorithm, and output the user feature;

receiving, by the computing device, an informed advisor element relating an informed advisor to the user feature, wherein receiving an informed advisor element comprises training, using element training data comprising a plurality of user features and a plurality of correlated informed advisor elements, a machine-learning model configured to receive the user feature as an input and output the informed advisor element, wherein the computing device is configured to iteratively update the element training data to reflect geographical variances among correlations between the plurality of user features and ad visor elements;

generating, by the computing device, an informed advisor grouping element as a function of the informed advisor element, wherein generating further comprises:

receiving a grouping training set, the grouping training set relating an informed advisor to an advisor review score; and calculating the informed advisor grouping element as a function of the grouping training set using an advisor machine-learning process, the advisor machine-learning process trained using the grouping training set;

determining, by the computing device, as a function of the informed advisor grouping element, a group compatible element;

grouping, by the computing device, an informed advisor of a plurality of informed advisors as a function of the group compatible element to enhance the user feature; and display, by the computing device, the group compatible element on a graphical user interface.

11. The method of claim 10, wherein receiving the informed advisor element further comprises:

receiving an element of informed advisor expertise;

locating an informed advisor who engages the expertise; and retrieving the informed advisor element as a function of locating the informed advisor who engages the expertise.

12. The method of claim 10, wherein the advisor review score further comprises:

receiving an informed advisor review from a review databank;

determining, using a validation machine-learning process, the validity of the review as a function of a validation training set, wherein the validation training set relates a review indicator to an authenticity score of a review; and generating the review score as a function of the informed advisor review.

13. The method of claim 12, wherein the review databank comprises a review platform containing a user generated review.

14. The method of claim 12, wherein the validation training set is retrieved from an online web service.

15. The method of claim 12, wherein authenticity score consists of a likelihood for a review to be validated.

16. The method of claim 10, wherein the group compatible element identifies the compatibility of a first informed advisor to a second informed advisor.

17. The method of claim 10, wherein determining the group compatible element further comprises:
   displaying on the computing device a plurality of elements describing an informed advisor group quality;
   receiving a user entry ranking the plurality of elements; and
   selecting an informed advisor group quality as a function of the ranked plurality of elements.

18. The method of claim 17, wherein selecting the informed advisor group quality further comprises:
   generating a loss function utilizing the ranked plurality of elements and the informed advisor group quality;
   calculating a difference between the ranked plurality of elements and the informed advisor group quality as a function of minimizing the loss function; and
   determining an informed advisor group compatibility for the user as a function of calculating the difference.

\* \* \* \* \*